(12) United States Patent
Schmidt et al.

(10) Patent No.: US 6,357,589 B2
(45) Date of Patent: *Mar. 19, 2002

(54) PACKAGING OF CATHETER PRODUCTS

(75) Inventors: Philip D. Schmidt, Arlington, TX (US); Adel Kafrawy, Kingston, MA (US)

(73) Assignee: Ethicon, Inc., Somerville, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/733,769

(22) Filed: Dec. 8, 2000

Related U.S. Application Data

(62) Division of application No. 09/267,148, filed on Mar. 11, 1999, now Pat. No. 6,186,325.

(51) Int. Cl.⁷ .............................................. B65D 83/10
(52) U.S. Cl. ..................... 206/364; 206/484.1; 206/439; 206/480
(58) Field of Search ............................... 206/364, 484.1, 206/439, 478, 365, 480, 379, 438; 220/4.01, 822, 826, 837

(56) References Cited

U.S. PATENT DOCUMENTS

| | | | | |
|---|---|---|---|---|
| 3,434,587 A | * | 3/1969 | Ciampa | 206/365 |
| 4,022,324 A | * | 5/1977 | Schuster | 206/439 |
| 4,113,090 A | * | 9/1978 | Carstens | 206/365 |
| 4,671,408 A | * | 6/1987 | Raines et al. | 206/365 |
| 4,892,525 A | * | 1/1990 | Hermann, Jr. et al. | 604/263 |
| 4,921,096 A | * | 5/1990 | McFarlane | 206/363 |
| 4,927,018 A | * | 5/1990 | Yang et al. | 206/365 |
| 5,205,408 A | * | 4/1993 | Cobb | 206/364 |
| 5,217,114 A | * | 6/1993 | Gadberry et al. | 206/364 |
| 5,246,109 A | * | 9/1993 | Markle et al. | 206/363 |
| 5,418,022 A | * | 5/1995 | Anderson et al. | 428/35.2 |
| 5,672,883 A | * | 9/1997 | Reich | 206/507.1 |

* cited by examiner

*Primary Examiner*—Shian Luong
(74) *Attorney, Agent, or Firm*—Blakely, Sokoloff, Taylor & Zafman

(57) ABSTRACT

According to one aspect of the invention, a medical package is provided which includes a housing, and a catheter product. The housing defines an enclosure which is sealed against ingress of contaminants. The housing has at least a first part and a second part which is movable relative to the first part to open the enclosure. At least one of the parts has a plurality of pores through which a sterilization fluid can enter the enclosure, but which substantially prevent entry of contaminants into the enclosure. The catheter product includes a body, and a vascular access member. The vascular access member has a first end and a second, vascular entry end. The first end is secured to the body and the second end is located distant from the body. The catheter product is located entirely within the enclosure. The catheter product is secured in position to the housing. The catheter product is removed from the housing after the second part is moved relative to the first part to open the enclosure.

31 Claims, 10 Drawing Sheets

PACKAGING OF CATHETER PRODUCTS

This application is a divisional application of the U.S. patent application Ser. No. 09/267,148, filed Mar. 11, 1999, now U.S. Pat. No. 6,186,325.

BACKGROUND OF THE INVENTION

1). Field of the Invention

This invention relates to packaging of catheter products.

2). Discussion of Related Art

Catheter products are increasingly used for gaining entry into internal target sites, for example for gaining entry into a lumen or other vascular of a person, and for passing diagnostic, therapeutic or other agents into or removing fluids from the internal target sites.

A catheter product of this kind usually includes a body, and an elongate vascular access member having a first end secured to the body and a second end located distant from the body. The second end is inserted into a lumen or other vascular. Many catheter products have needles located in their vascular access members, the needles having sharp tips which are used for piercing a required area for purposes of gaining entry. On other catheter products the vascular access members themselves are needles which have second ends which are sharpened for purposes of gaining entry. Once entry is gained into a required internal target site, fluids can be passed through the vascular access member and the body to or from the internal target sites.

A catheter product is usually packaged by first inserting the vascular access member thereof through an opening in a sheath, followed by the body thereof. The body is then secured to the sheath so that the catheter product is located in a stationary position relative to sheath with the second end of the vascular access member located distant from an inner wall of the sheath. The sheath then provides the necessary structure to protect the vascular access member.

Once the catheter product is secured to the sheath, a portion of the body of the catheter product still protrudes from the opening in the sheath, thus potentially exposing the portion of the body protruding from the opening in the sheath to contamination. An interface between the body and the sheath is also usually not of the kind which prevents ingress of contaminants into that the sheath, thus potentially exposing the remainder of the catheter product, including the vascular access member, to contamination.

To prevent contamination, the sheath and the catheter product are subsequently loosely located within conventional blister packaging. The blister packaging provides an enclosure which is sealed against ingress of contaminants and prevents contamination of the sheath and catheter product. The catheter product, in effect, therefore has to be packaged twice, once to provide the required structural integrity to protect the vascular access member, and once more to prevent contamination.

SUMMARY OF THE INVENTION

According to one aspect of the invention, a medical package is provided which includes a housing, and a catheter product. The housing defines an enclosure which is sealed against ingress of contaminants. The housing has at least a first part and a second part which is movable relative to the first part to open the enclosure. At least one of the parts has a plurality of pores through which a sterilization fluid can enter the enclosure, but which substantially prevent entry of contaminants into the enclosure. The catheter product includes a body, and a vascular access member. The vascular access member has a first end and a second, vascular entry end. The first end is secured to the body and the second end is located distant from the body. The catheter product is located entirely within the enclosure. The catheter product is secured in position to the housing. The catheter product is removed from the housing after the second part is moved relative to the first part to open the enclosure.

The first part may be a hollow sheath with an opening providing access into the sheath. The catheter product may be at least partially located within the sheath and be secured to the sheath inside the sheath. The second part maybe a lid which closes the opening.

A lid may be attached to a periphery of the opening and the attachment between the lid and the periphery of the opening may be at least partially breakable.

The enclosure, formed by the sheath, may be relatively large in a first area near the opening and relatively small in a second area on a side of the first area opposing the opening. The body may be secured to the sheath in the first area, and the elongate needle member may be at least partially located in the second area.

The sheath may have a retaining formation extending from an inner surface thereof, and the body may have an engaging formation which engages with the retaining formation to support the catheter product in position.

The retaining formation may include first and second projections with a gap defined between them. At least one of the projections may be movable to the extent that it can give way under a force created by the engaging formation when the catheter product is inserted into the sheath, and at least partially return to its original position so as to lock the engaging formation in the gap.

The sheath may at least partially be made of a flexible material. The retaining formation may move away from the engaging formation when the sheath is flexed, thereby disengaging the engaging formation from the retaining formation so as to allow for removal of the catheter product from the sheath.

The medical package may include finger tabs on opposing side of the package sheath which, when contacted by two respective fingers on a hand of a person, and are moved relative to one another by the fingers, may cause movement of the retaining formation away from the engaging formation and disengagement of the engaging formation from the retaining formation.

The retaining formation may extend in a first selected direction from the inner surface. When the finger tabs are moved relative to one another, the sheath may be squeezed together transversely to the first selected direction, causing the retaining formation to move away from the engaging formation in a second selected direction, opposing the first selected direction, and disengagement of the engaging formation from the retaining formation.

The medical package may include flange portions extending from the sheath, and the finger tabs may be located on the flange portions.

The flange portions may pivot about first portions of the sheath and compress second portions of the sheath towards one another to cause elongation of at least part of the sheath in the second selected direction.

At least a first of the finger tabs may pivot about a first portion of the sheath, and the retaining formation may be located on a second portion of the sheath, and a side of the first portion approximately opposing the first finger tab, so that, when the first finger tab pivots about the first portion in a first pivoting direction, the retaining formation also pivots in the first pivoting direction about the first portion away from the engaging formation.

The sheath may include an additional retaining formation which engages with a retaining formation of the sheath. A second of the finger tabs may pivot about a third portion of the sheath. The additional retaining formation may be located on a fourth portion of the sheath on a side of the third portion approximately opposing the second finger tabs so that, when the second finger tab pivots about the third portion in a second pivoting direction, opposing the first pivoting direction, the additional retaining formation also pivots in the second direction away from the additional engaging formation.

The sheath may have a hinge portion between the retaining formations which, when the first finger tab pivots in the first pivoting direction and the second finger tab pivots in the second pivoting direction, assists in increasing an amount of rotation of the retaining formations relative to one another, resulting in more movement of the respective retaining formations away from the respective engaging formations.

The hinge portion may be formed so as to create a stress concentration which causes more flexing of the sheath.

The hinge portion may be a narrowing in the sheath.

The sheath may have at least first and second components. When the lid is at least partially removed, the second component may be movable relative to the first component to allow for better access to the medical product.

The retaining formation may be located on an inner wall of the sheath, and the body may have an engaging formation which engages with the first component. When the second component is moved relative to the first component to allow for better access to the medical product, the engaging formation may be engaged with the retaining formation.

The second component may hinge relative to the first component.

The sheath may have at least a third component which hinges relative to the first component to allow for better access to the medical product.

The opening may have at least two finger wells, on different sides of the catheter product. Fingers on a hand of a person may be insertable into the finger wells. The finger wells may be open towards the catheter product to allow for gripping of the catheter product and subsequent removal of the catheter product from the sheath.

The sheath may have first and second opposed wall portions having edges which partially define the opening, and the lid closing off the opening, wherein the edges are shaped so that, when the lid is at least partially moved to open the enclosure, there is a line of sight through the sheath between the wall portions of the sheath, the line of sight being at least partially blocked by the catheter product.

The opening may be formed so that, when the lid is at least partially moved to open the enclosure, a portion of the medical product may be exposed when viewed in a direction at right angles to a center line of the medical product.

The second end is preferably displaced from an inner wall of the housing.

A sharp tip is preferably located at the second end.

The vascular access member is preferably a needle and the second end is a sharp tip of the needle. The medical package may further include a catheter assembly which includes a hollow hub and a catheter. The catheter has a first end secured to the hub and a second end located distant from the hub. The hub and catheter are located over the needle with the catheter located on a side of the hub opposing the body. The housing may have a shelf on an inner surface thereof which supports the hub on a surface thereof opposing the body.

The invention also provides a medical package which includes a housing and a catheter product. The housing defines an enclosure which is sealed against ingress of contaminants. The housing has a hollow elongate sheath with an end having an opening into the sheath. The lid closes the opening and seals with a periphery of the opening. The catheter product includes a body, and a vascular access member. The vascular access member has a first end and a second, vascular entry end. The first end is secured to the body and the second end is located distant from the body. The catheter product is located entirely within the sheath.

The invention also provides a method of packaging a catheter product. The catheter product is located within a housing. The housing defines an enclosure which is sealed against ingress of contaminants and has at least one part having a plurality of pores through which a sterilization fluid can enter the enclosure, but which substantially prevent entry of contaminants into the enclosure. The medical product is located entirely within the enclosure. The medical product has a body secured in position to the housing, and a vascular access member having a first end and second, vascular entry end. The first end is secured to the body and the second end is located distant from the body in a position which is displaced from an inner wall of the housing.

BRIEF DESCRIPTION OF THE DRAWINGS

The invention is further described by way of examples with reference to the accompanying drawings wherein.

DETAILED DESCRIPTION OF THE INVENTION

A number of embodiments of a medical package according to the invention are described. In each case, the medical package includes a housing defining an enclosure which is sealed against an ingress of contaminants, and a catheter product. The housing includes an elongate sheath with an opening in an end providing access into the sheath, and a lid which closes the opening. The lid is made of a breathable material which allows for a sterilization fluid to enter the enclosure, but which prevents contaminants from entering the enclosure. The catheter product is of the kind which includes a body, and a needle having one end secured to the body and an opposing, sharp vascular entry end. The catheter product is located in a stationary position relative to the sheath by mounting the body releasably to the sheath. The sheath so provides the necessary structural rigidity to prevent damage to the entire catheter product, and forms part of a housing which encloses the catheter product so that the catheter product is prevented from being contaminated.

Figure 1:
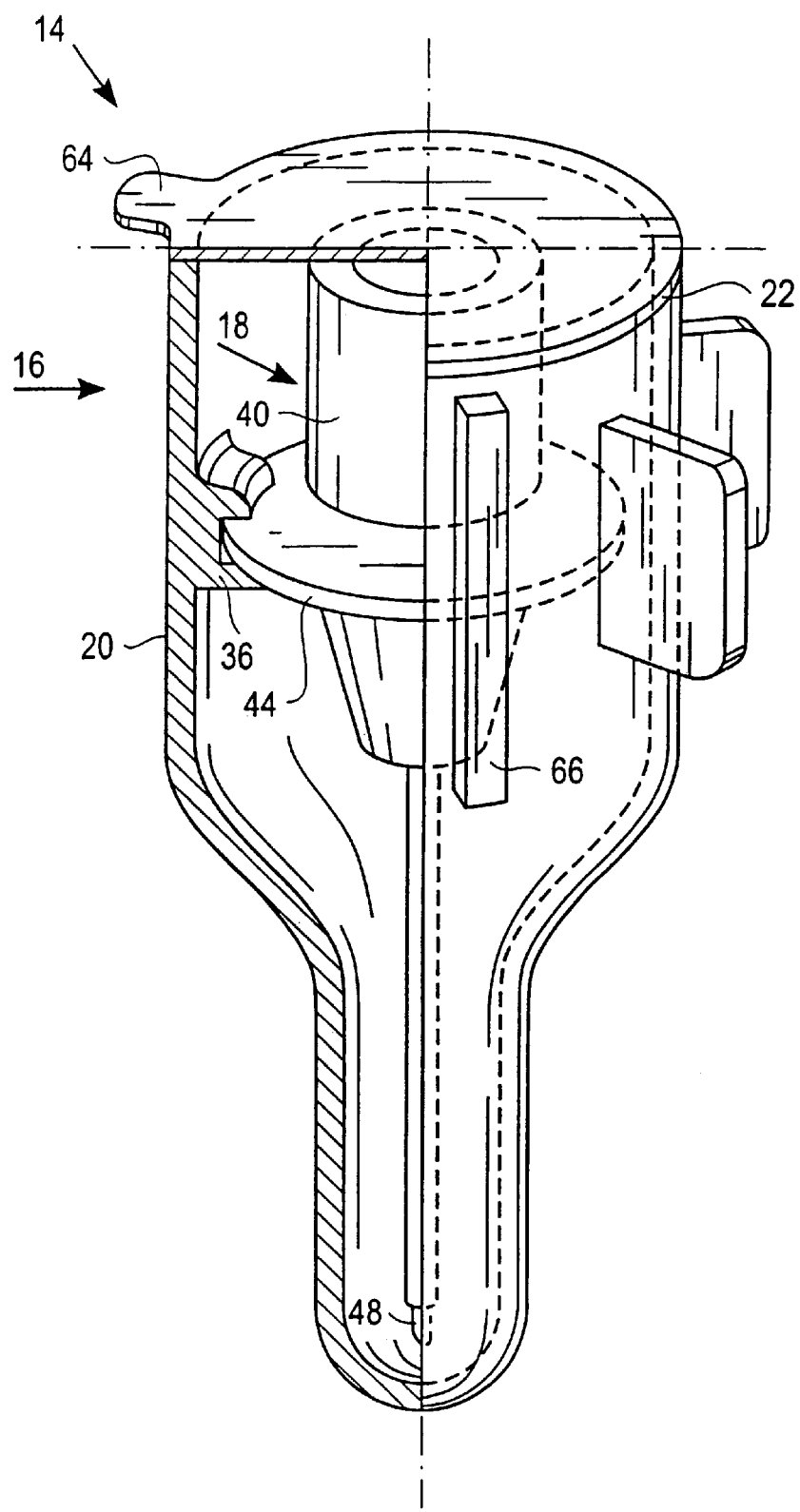
FIG. 1 is a partially sectioned perspective view of a medical package according to one embodiment of the invention.

FIG. 1 of the accompanying drawings illustrates a medical package 14 according to one embodiment of the invention. The medical package 14 includes a housing 16, and a catheter product 18 located within the housing 16.

Figure 2:
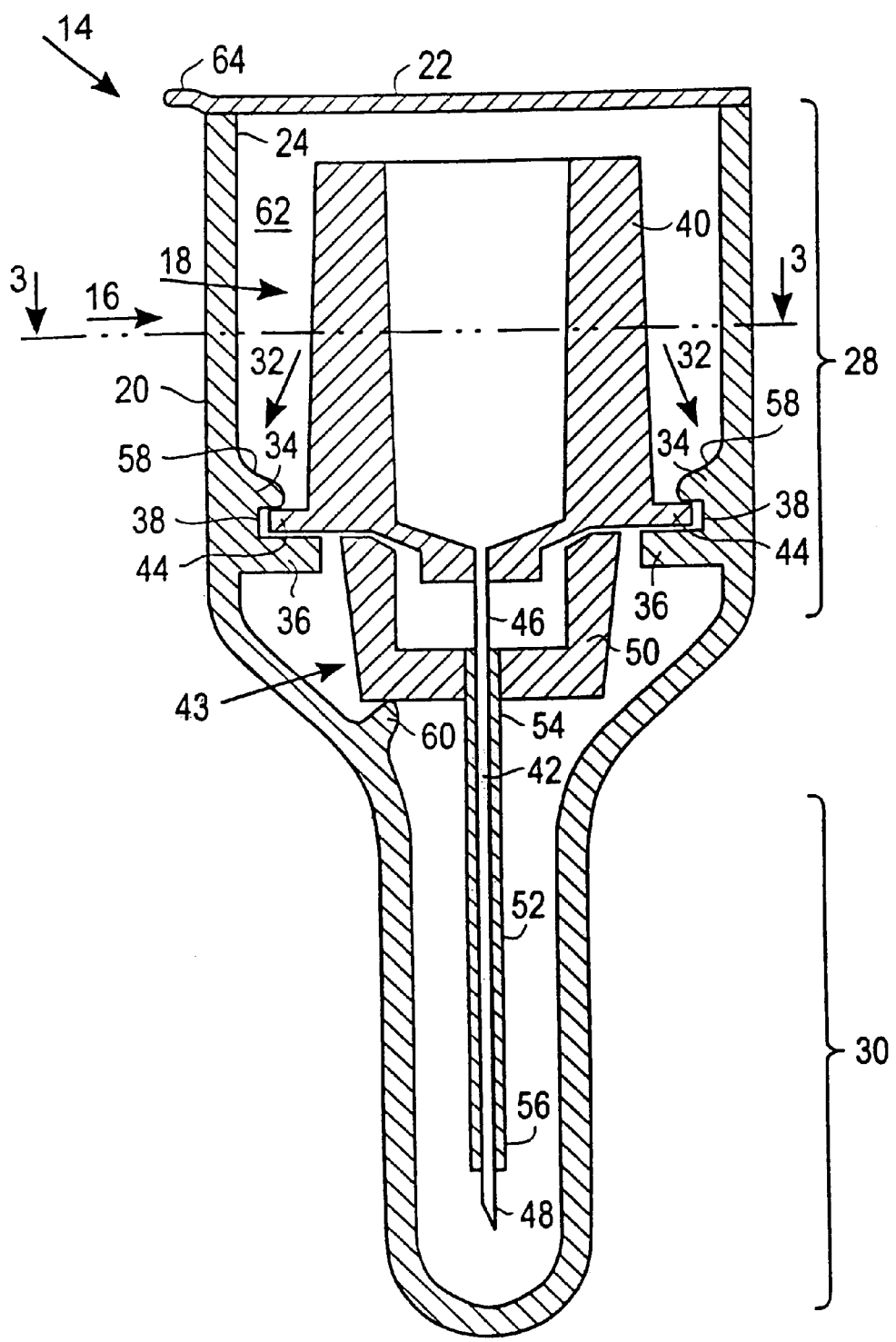
FIG. 2 is a cross-sectional side view of the medical package of FIG. 1.

FIG. 2 illustrates the medical package 14 in cross-sectional detail. The housing 16 includes an elongate hollow sheath 20 and a lid 22.

The sheath 20 has an opening 24 at the upper end thereof which provides access into the sheath 20. The sheath 20 is relatively large in a first area 28 near the opening 24, and relatively small in a second area 30 on a side of the first area 28 opposing the opening 24.

The sheath 20 has a plurality of retaining formations 32 extending from an inner surface thereof within the first area 28. Each retaining formation 32 includes first and second projections, 34 and 36 respectively, with a gap 38 defined between the first and second projections 34 and 36.

The lid 22 is made of a breathable material which is sold under the name "TYVEK" by Dupont. The breathable material typically has pores which are about 0.2 microns in diameter.

The catheter product 18 includes a body 40, an elongate vascular access member or needle 42, and a catheter assembly 43.

The body 40 has an annular engaging formation 44 extending from an outer surface thereof. The needle 42 has a first end 46 and a second, vascular entry end 48. The first end 46 is secured to the body 40 and second end 48 is located distant from the body.

The catheter assembly 43 includes a hub 50, and a catheter 52. The first end 54 of the catheter 52 is secured to the hub 50 and a second, opposing end 56 of the catheter 52 is located distant from the hub 50. The second end 45 of the needle 42 is inserted through the hub 50, and from the hub 50 through the catheter 52 until the second end 48 of the needle 42 protrudes out of the second end 56 of the catheter 52.

The second end 48 of the needle 42 has a sharp tip which may be used for piercing a vascular such as a vein or an artery. The catheter 52 and the needle 42 are then inserted into the vascular. Fluid within the vascular passes through the needle 42 into the body 40. The body 40 is usually transparent so that the fluid is visible through the body 40. The needle 42 is then removed from the catheter 52 and another device such as a syringe or a pipe of a drip is connected to the hub 50. Fluids can be passed between the other device and the vascular through the hub 50 and the catheter 52.

The medical package 14 is assembled by first inserting the catheter product 18 through the opening 24 into the sheath 20. The needle 42 is inserted first into the sheath 20, followed by the body 40. The first projections 34 are spaced relative to one another more closely than an outer diameter of the engaging formation 44 so that the engaging formation 44 is brought into contact with sloped upper surfaces 58 of the first projections 34. When the catheter product 18 is further inserted into the sheath 20, the engaging formation 44 creates outward forces acting on the sloped upper surfaces 58.

The sheath 20 is made of a flexible material such as polypropylene or nylon and, due to its materials and construction, flexes under the force created by the engaging formation 44 so that the spacing between the first projections 34 widens. Once the spacing between the first projections 34 widens, the engaging formation 44 passes through the first projections 34 and comes to rest against the second projections 36. Due to the flexibility of the sheath 20, the first projections 34 then return to their original positions in a snapping action. Once the first projections 34 have returned to their original positions, the engaging formation 44 is locked within the gaps 38.

By locking the engaging formation 44 within the gaps 38, the catheter product 18 is mounted to the sheath 20 and supported in a stationary position relative to the sheath 20. The catheter product 18 is entirely located in the sheath 20 and the sheath 20 is sufficiently strong to protect the catheter product 18. The body 40 is located in the first area 28 of the sheath 20. The needle 42 is almost entirely located in the second area 30 of the sheath 20 with the second end 48 and the sharp tip 56 both displaced from an inner wall of the sheath 20.

A retaining shelf 60 is located on an inner sheath 20. The hub 50 has a surface on opposing sides thereof and the body 30 which rests on the shelf 60. The shelf 60 so prevents the catheter assembly 43 from moving off the needle 42.

The lid 22 is then positioned so that it closes off the opening 24 and is then heated so that a periphery thereof seals circumferentially on a periphery of the opening 24 and is attached to a periphery of the opening 24. The sheath 20 and the lid 22 so jointly define an enclosure 62 which is sealed against ingress of contaminants.

Because of the porous nature of the lid 22, a sterilization fluid such as ethylene oxide gas may be introduced into the enclosure 62 so that the confines of the enclosure 62 may be sterilized. The pores within the lid 22 are, however, generally too small for contaminants or microorganisms to pass through so that the confines of the enclosure 62 remain sterile.

The housing 16 of FIG. 1 and FIG. 2 provides a rigid and sturdy enclosure which entirely encloses the catheter product 18 and supports the catheter product 18. There is therefore no need for additional packaging such as blister packaging to seal the housing 16 against ingress of contaminants. The medical package 14 can thus be provided to a user substantially in the form shown in FIG. 1 and FIG. 2.

The lid 22 has a tab 64 which can be pulled so that the attachment between the periphery of the lid 22 and the periphery of the opening 24 is broken. The lid 22 can so be removed from the sheath 20 so that the enclosure 62 is opened to provide access to the catheter product 18.

Removal of the catheter product 18 from the sheath 20 is now discussed with reference to FIG. 3 and FIG. 4.

Figure 3:
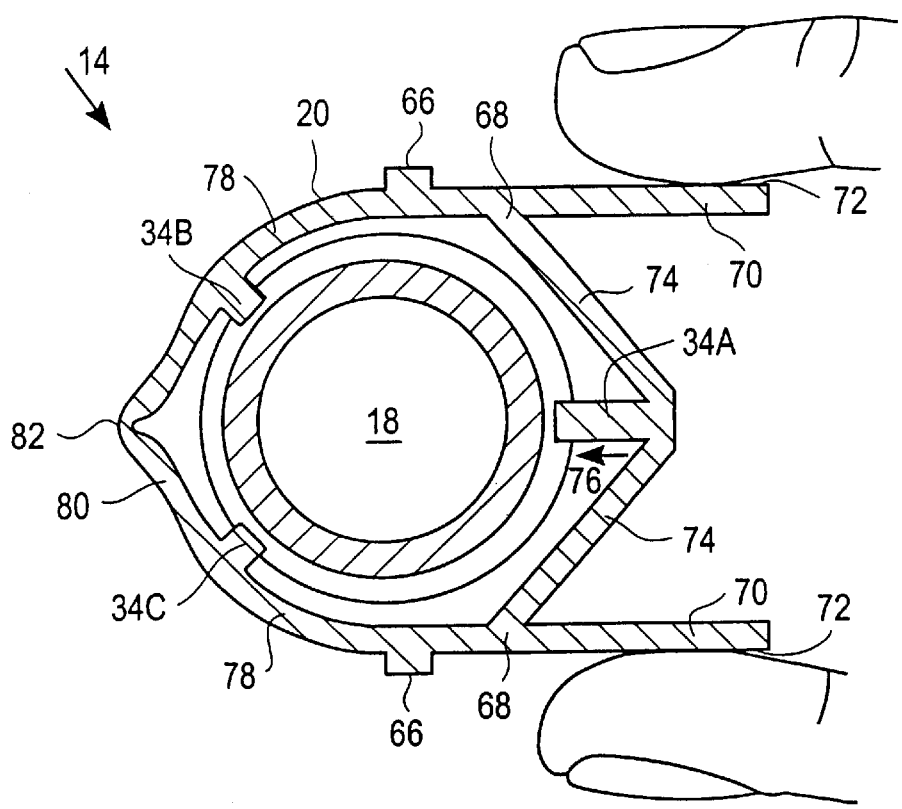
FIG. 3 is a cross-sectional view on 3—3 in FIG. 2.

FIG. 3 illustrates the medical package 14 in cross section on 3—3 in FIG. 2. The sheath 20 includes strengthening first portions, or ribs 66 on opposing sides thereof. The sheath 20 extends from each rib 66 to respective second portions 68 thereof. Third, flange portions 70 extend from the second portions 68 away from the sheath 20. The flange portions 70 are substantially parallel to one another and finger tabs 72 are located on outer surfaces of the flange portions 70.

The sheath 20 includes fourth portions 74 extending from the second portions 68 and coming together at one of the first projections 34A (of one of the retaining formations 32). The first projection 34A extends from an inner surface of the sheath 20 in a first selected direction 76 to engage with the catheter product 18.

Fifth portions 78 of the sheath 20 extend from the ribs 66 to more of the first projections 34B and 34C. The respective first projections 34B and 34C are located on sides of the ribs 66 approximately opposing the finger tabs 72. The first projections 34B and 34C also extend from an inner surface of the sheath 20 to engage with the catheter product 18.

A sixth portion 80 of the sheath 20 extends from the first projection 34B to the first projection 34C. The sixth portion 80 includes a hinge portion 82 located about halfway between the first projection 34B and the first projection 34C. The hinge portion 82 is a narrowing in the sixth portion 80.

To remove the catheter product 18 from the sheath 20, the medical package 14 is first inverted so that the opening 24 is at the bottom. The finger tabs 72 are spaced from one another so that a person may easily engage first and second fingers on one hand, for example a thumb and a forefinger, with the respective finger tabs 72.

Figure 4:
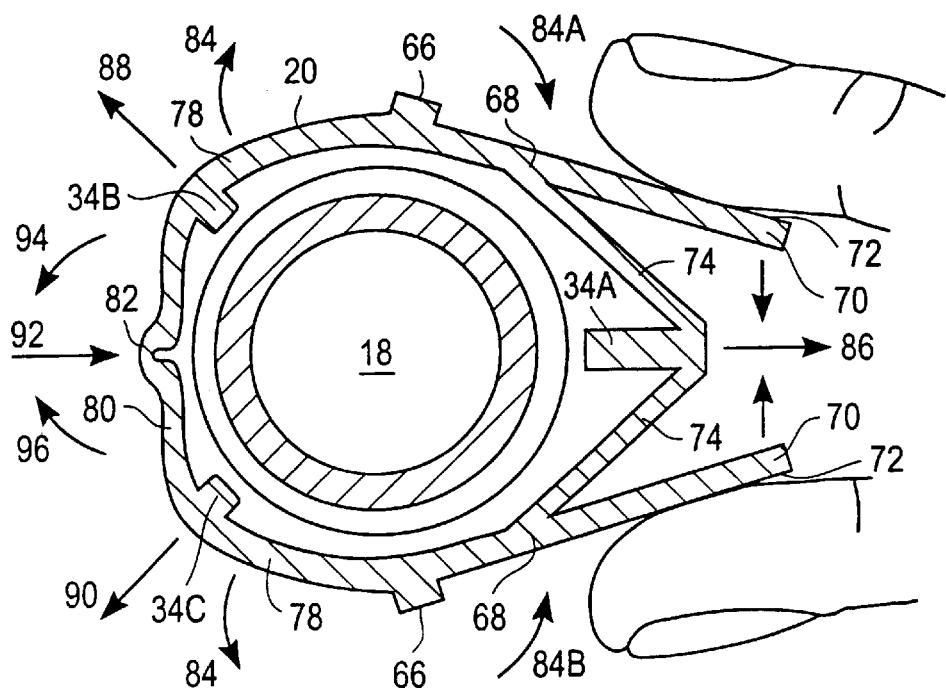
FIG. 4 is a view similar to FIG. 3 illustrating release of a catheter product from a sheath of the medical package.

As shown in FIG. 4, the person may then squeeze the flange portions 70 towards one another in a direction transversely to the first selected direction 76. The flange portions 70 pivot about the ribs 66 in first and second pivoting directions 84A and 84B respectively, thereby compressing the second portions 68 towards one another. The second portions 68 act on the fourth portions 74 to cause flexing and elongation of the sheath 20 in a second selected direction 86 opposing the first selected direction 76. The elongation, or flexing of the sheath 20 in the second selected direction 86 results in movement of the first projection 34A in the second selected direction 86 away from the catheter product 18, and disengagement thereof from the catheter product 18.

The fifth portions 78 pivot together with the flange portions 70 in the first and second pivoting directions 84A and 84B so that the first projections 34B and 34C also move away from the catheter product 18, in third and fourth directions 88 and 90 respectively, when the flange portions 70 are squeezed together, resulting in disengagement of the first projections 34B and 34C from the catheter product 18.

Movement of the first projections 34B and 34C in the third and fourth directions 88 and 90 cause movement of the sixth portion 80 towards the catheter product 18, or shortening of the sheath 20 in a fifth direction 92. A stress concentration is created within the hinge portion 82 which assists in bending of the sixth portion 80 in the region of the hinge portion 82. Assisted bending of the sixth portion 80 in region of the hinge portion 82 results in more rotation, or "hinging", of the first projection 34B in a direction 94 about the hinge portion 82, and of the first projection 34C in a direction 96 about the hinge portion 82. Because of more hinging of the first projections 34B and 34C about the hinge portion 82, movement of the first projections 34B and 34C in the third and fourth directions 88 and 90 is enhanced and disengagement of the first projections 34B and 34C from the catheter product 18 is assisted.

Once the first projections 34A, 34B, and 34C are disengaged, the catheter product 18 simply drops out of the sheath 20 through the opening 24. Referring again to FIG. 2,
the sheath 20 flexes at the first area 28 but not in the second area 30. There is thus no danger of damaging the needle 42 when the sheath is flexed to remove the catheter product 18. The wall thickness of the sheath in the second area 30 may be made thicker than the wall thickness in the first area 28 so that the sheath can flex sufficiently in the first area 28, but add extra protection for the needle in the second area 30.

It can be seen from the aforegoing description that the catheter product 18 is entirely located within the sheath 20 even after the lid 22 is removed, thus substantially reducing risk of contamination of the catheter product 18 even after the lid 22 is removed. The catheter product 18 is then removed from the sheath 20 without the need for touching the catheter product 18 and therefore with substantially reduced risk of contamination of the catheter product 18. By contrast, the embodiments herein after described all make provision for accessibility of catheter products so that the catheter products can be manually removed. In the descriptions of the embodiments which follow, for purposes of efficacy, not all details thereof are described and discussed in detail. Instead, the description of each of the embodiments which follow primarily indicates differences between the specific embodiment described and an embodiment or embodiments which have been described previously. Unless specifically stated otherwise or unless it can be inferred, therefore, it can be assumed that the details of subsequent embodiments are the same as details of embodiments which have been described previously. In particular, the catheter product of the embodiment wherein after described is the same as the catheter product 18 of FIG. 1 and in each case includes a catheter assembly such as the catheter assembly 43 of FIG. 1. The catheter assemblies are supported in a manner similar to a manner in which the shelf 60 support the catheter assembly 43 as illustrated in FIG. 2.

Figure 5:
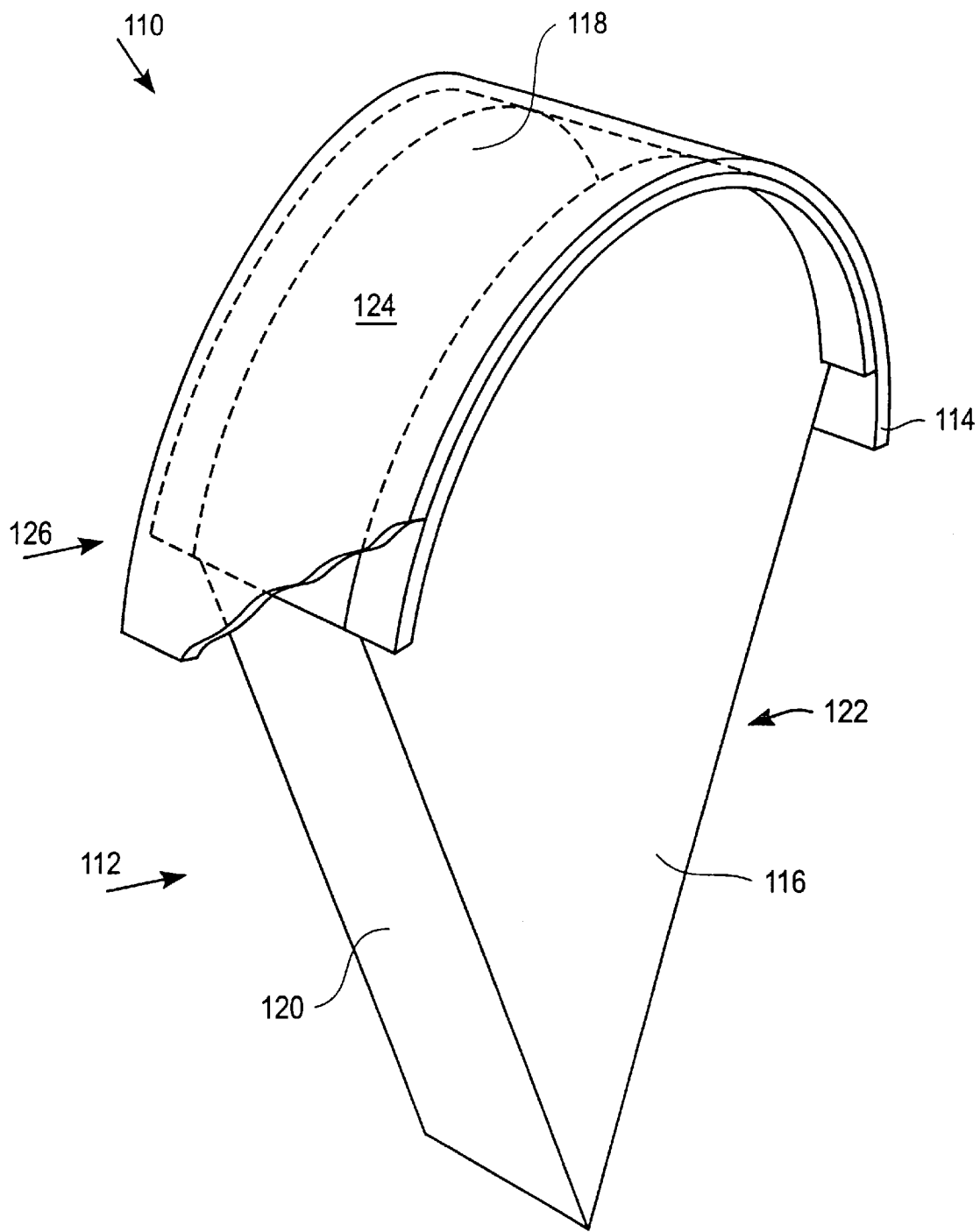
FIG. 5 is a perspective view of a housing of a medical package according to an alternative embodiment of the invention.

FIG. 5 illustrates a housing 110 of a medical package according to one alternative embodiment of the invention. The housing 110 includes a sheath 112 and a lid 114.

The sheath 112 includes first, second, third, and fourth walls 116, 118, 120, and 122 respectively. The first and second walls 116 and 118 oppose one another and the third and fourth walls 120 and 122 oppose one another. Upper peripheries of the walls 116, 118, 120, and 122 define a periphery of an opening 124 into the sheath 112.

The lid 114 may be of the kind hereinbefore described with reference to FIG. 1 and FIG. 2 and is secured over the opening 124 in a similar manner. Upper peripheries of the first and second walls 116 and 118 are curved so that, when the lid 114 is removed, there is a line of sight in a direction 126 through the sheath 112 between upper portions of the walls 116 and 118.

Figure 6:
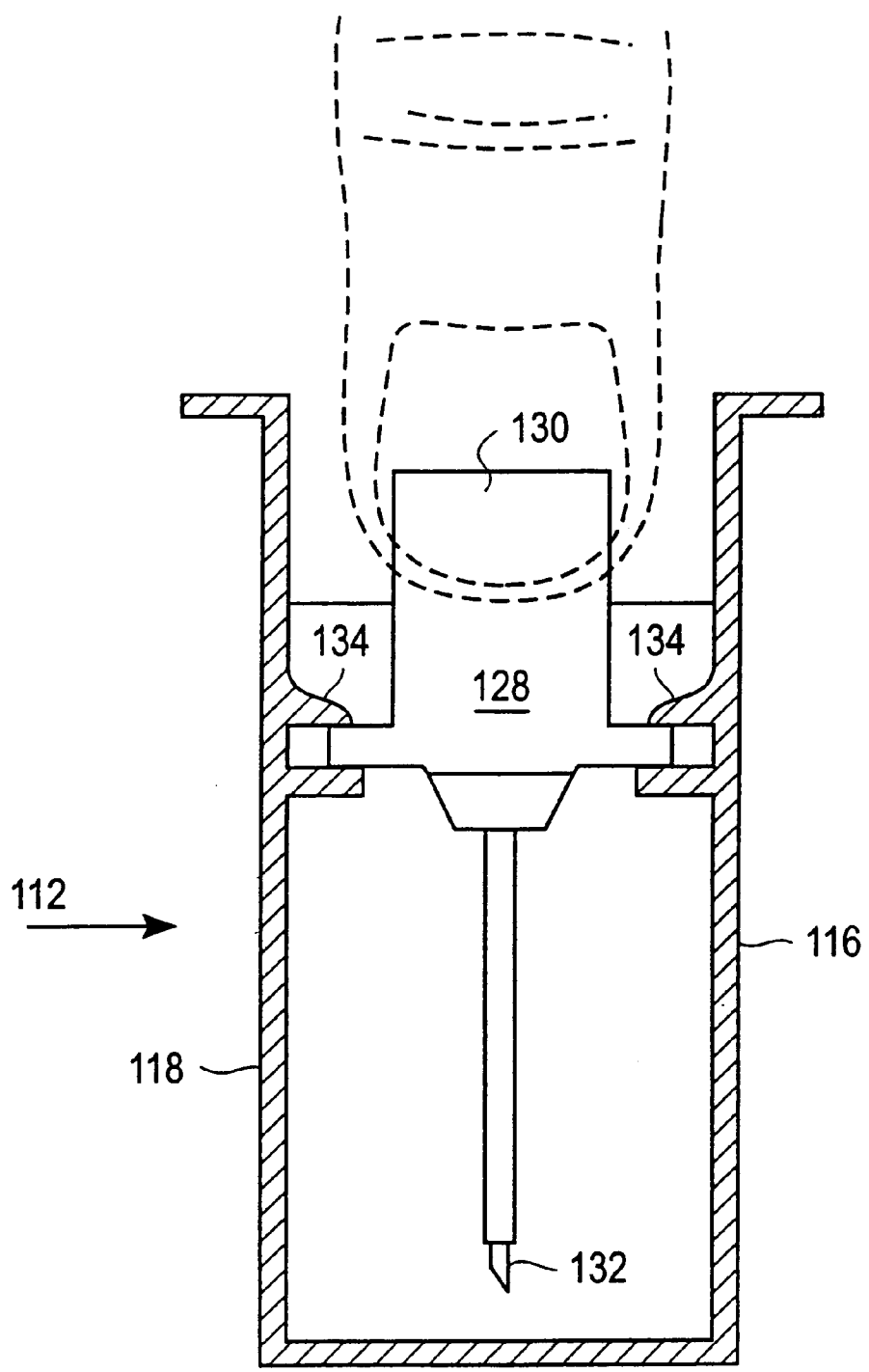
FIG. 6 is a cross-sectional end view of the housing of FIG. 5, further illustrating a catheter product secured within the housing.

FIG. 6 shows the sheath 112 in cross section when viewed in the direction 126 of FIG. 5. A catheter product 128 is mounted between the first and second walls 116 and 118 in a manner similar to the manner in which the catheter product 18 of FIG. 1 and FIG. 2 is mounted to the sheath 20. The line of sight through of the sheath 112 between upper portions of the first and second walls 116 and 118 is blocked by a portion of a body 130 of the catheter product 128, while the remainder of the body 130 and a needle 132 of the catheter product 128 are entirely located within the sheath 112. An upper portion of the body 130 thus protrudes above a portion of an upper periphery of the opening 124. The upper portion of the body 130 is therefore accessible and can be gripped between two fingers. The catheter product 128 can then be pulled from the sheath 112 with retaining formations 134 giving way under a force created when the catheter product 128 is pulled out of the sheath 112.

When the sheath 112, the catheter product 128 and the lid 114 are assembled, a medical package is provided which is assembled in the same manner, made of the same materials, and is the same as the medical package 14 of FIG. 1 and FIG. 2 in all other respects.

Figure 7:
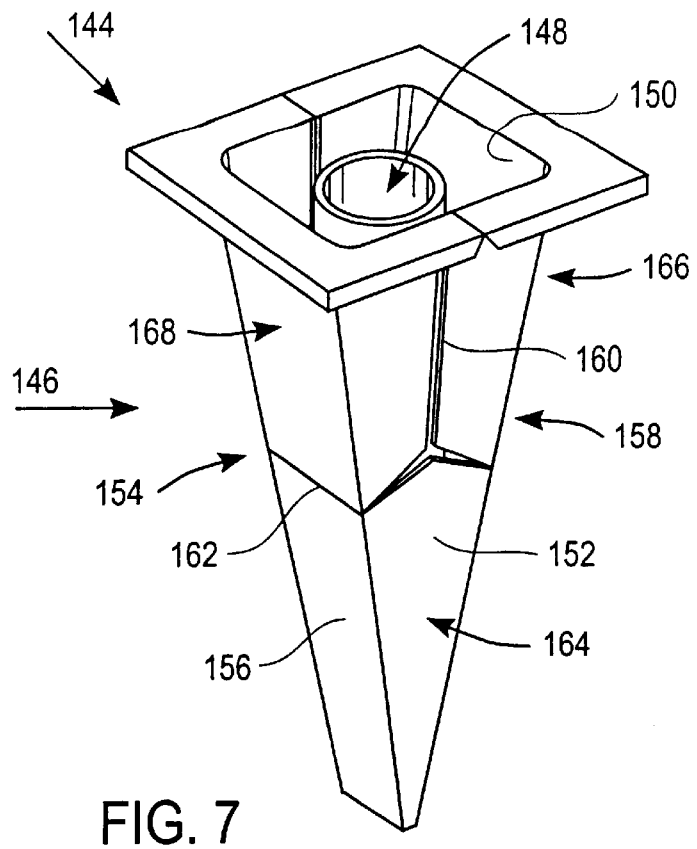
FIG. 7 is a perspective view illustrating a part of a medical package according to a further embodiment of the invention.

FIG. 7 illustrates a part of a medical package 144 according to a further embodiment of the invention. The medical package 144 includes a sheath 146 and a catheter product 148 located within the sheath 146. As with the embodiment of FIG. 1 and FIG. 2, the sheath 146 has an opening 150 which is closed off by a lid (not shown) so that the sheath 146 and the lid jointly define an enclosure for the catheter product 148.

The sheath 146 is initially a single component having first, second, third, and fourth walls 152, 154, 156, and 158 respectively with the first and second walls 152 and 154 opposing one another and the third and fourth walls 156 and 158 opposing one another. Breakable lines 160 are formed in the first and second walls 152 and 154 and hinge lines 162 (also shown in FIG. 13) are formed in the third and fourth walls 156 and 158. The breakable lines 160 and the hinge lines 162 divide the sheath 146 into a first, lower component 164, a second, upper component 166, and a third, upper component 168. It should be noted that the breakable lines 160 do not go through into the sheath 146, but are merely lines that are formed on the sheath 146 to weaken the sheath 146 in selected areas.

Figure 8:
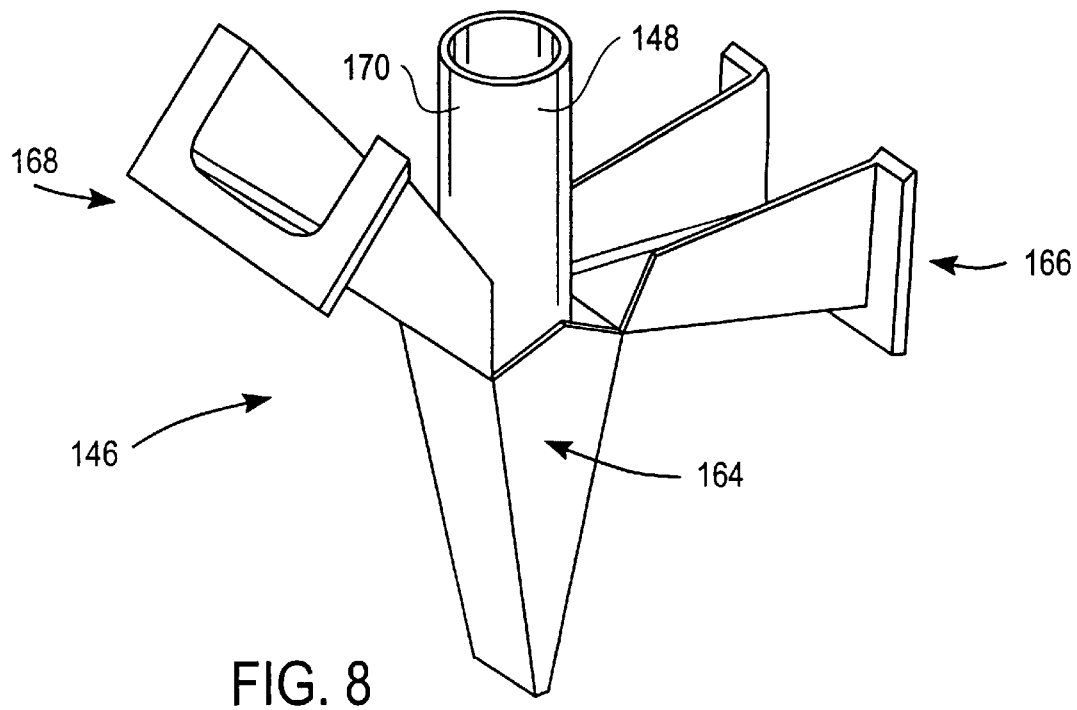
FIG. 8 is a view similar to FIG. 7 after a housing of the medical package is broken open.

Once the lid is removed from the opening 150, the catheter product 148 is still entirely located within the sheath 146. The second and third components 166 and 168 can be pulled apart so that the sheath 146 breaks open along the breakable lines 160 and the second and third components hinge relative to the first component 164 at the hinge lines 162, as illustrated in FIG. 8. An upper portion of a body 170 of the catheter product 148 is then accessible while another portion (not shown) of the body 170 is located within the first component 164 and is mounted thereto in a manner similar to the manner in which the body 40 is mounted to the sheath 20 as illustrated in FIG. 2. A person can thus grip the upper portion of the body 170 and pull the catheter product 148 out of the first component 164 of the sheath 146.

Figure 9:
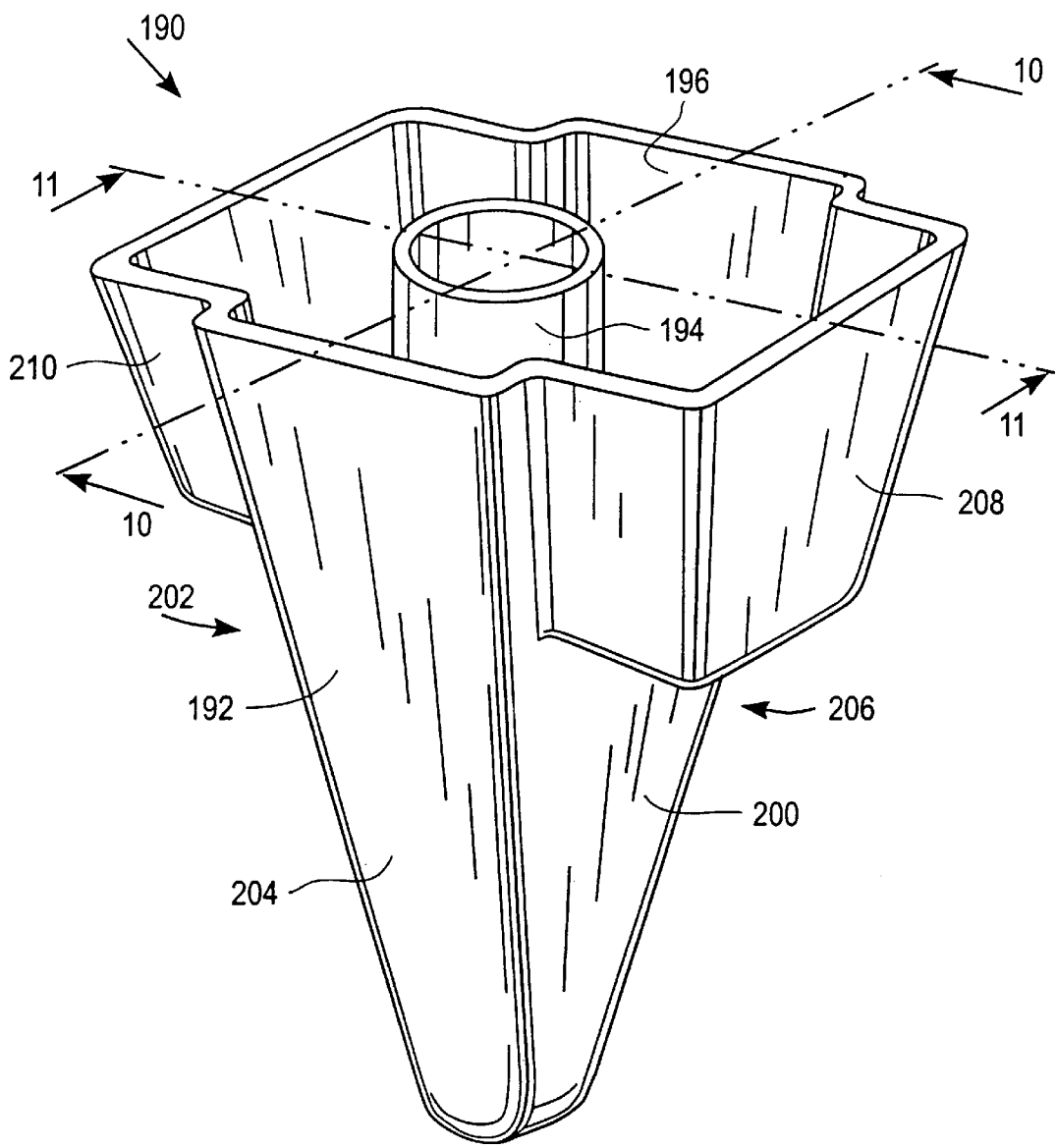
FIG. 9 is a perspective view of the part of a medical package according to yet a further embodiment of the invention.

FIG. 9 illustrates a part of a medical package 10 according to yet a further embodiment of the invention. The medical package 190 includes a sheath 192, a lid (not shown), and a catheter product 194 located within the sheath 192. The sheath 192 has an opening 196 through which the catheter product 194 is inserted into the sheath 192. The catheter product 194 is secured to the sheath 192 in a manner similar to the manner in which the catheter product 18 is secured to the sheath 20 as illustrated in FIG. 2 and the lid closes off the opening 196 and is secured thereto in a manner similar to the manner in which the lid 22 closes off and is secured over the opening 24 as illustrated and described with reference to FIG. 2.

The sheath 192 has first, second, third, and fourth walls 200, 202, 204, and 206, the first and second walls 200 and 202 opposing one another and the third and fourth walls 204 and 206 opposing one another. The first and second walls 200 and 202 each include a respective finger well 208 and 210.

Figure 10:
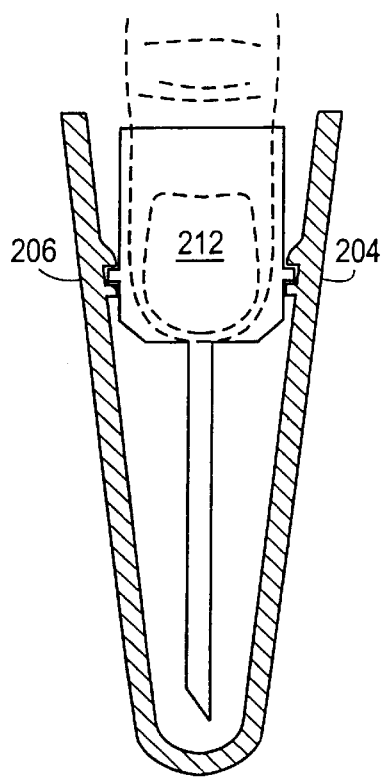
FIG. 10 is a cross-sectional side view on 10—10 in FIG. 9.
Figure 11:
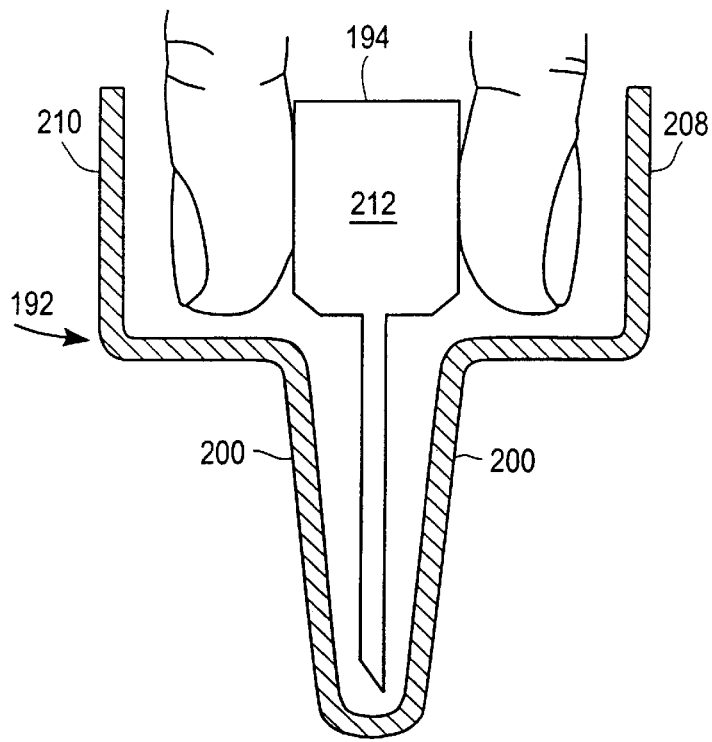
FIG. 11 is a cross-sectional side view on 11—11 in FIG. 9.

FIG. 10 is a cross-sectional view on 10—10 in FIG. 9 and FIG. 11 is a cross-sectional view on 11—11 in FIG. 9. FIG. 10 illustrates that the body 212 is mounted between the third and fourth walls 204 and 206 in a manner similar to the manner in which the body 40 is mounted to the sheath 20 as illustrated and described with reference to FIG. 2. As more particularly shown in FIG. 11, a person can insert first and second fingers into the finger wells 208 and 210 and the finger wells 208 and 210 are open towards the body 212 of the catheter product 194 to allow for gripping of the body 212 and subsequent removal of the catheter product 194 from the sheath 192.

Figure 12:
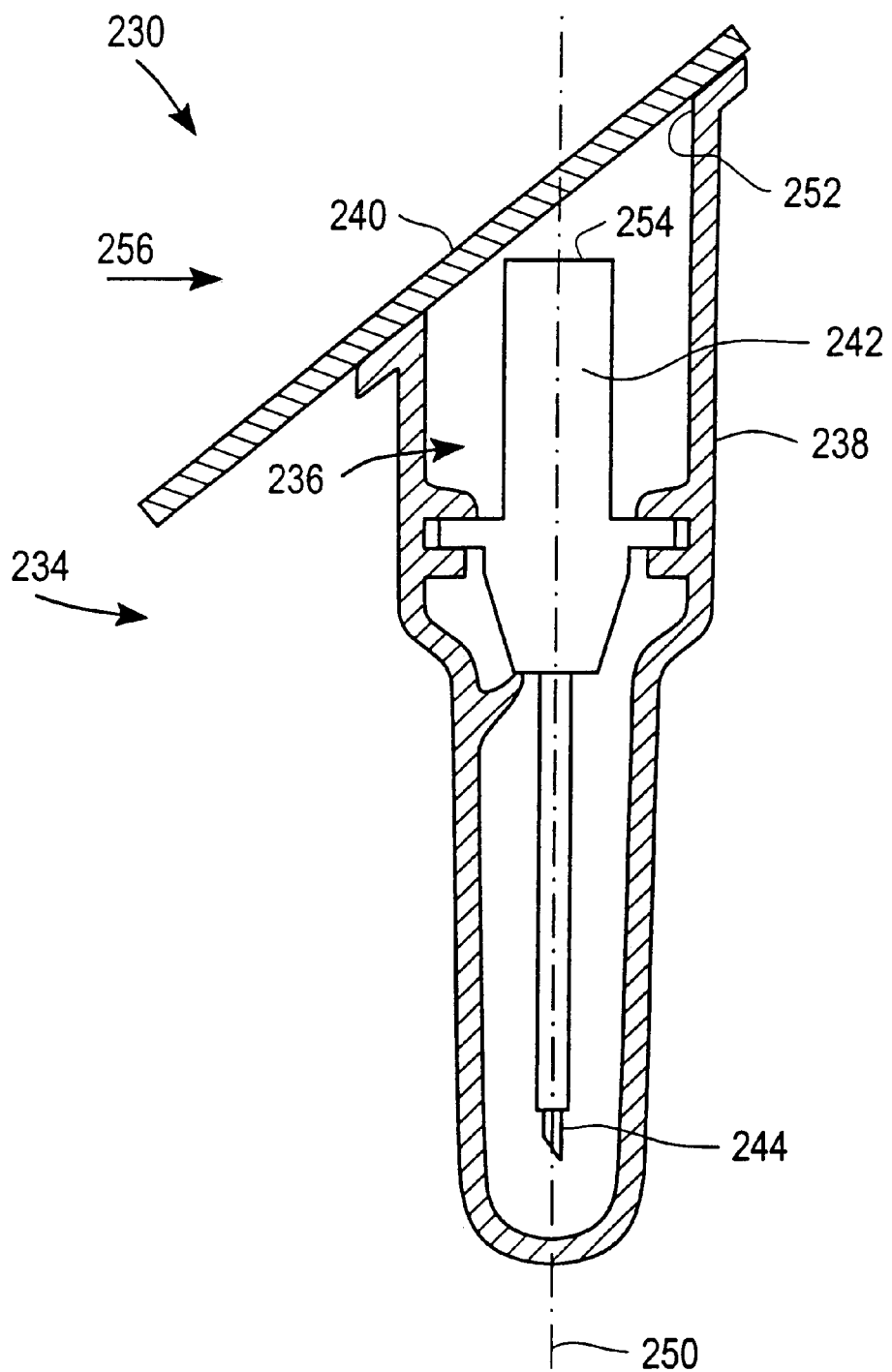
FIG. 12 is a cross-sectional side view of a medical package according to yet a further embodiment of the invention.

FIG. 12 illustrates a medical package 230 according to yet a further embodiment of the invention. The medical package 230 includes a housing 234 and a catheter product 236 located within the housing 234. As with the previous embodiments, the housing 234 includes a sheath 238 and a lid 240, and the catheter product 236 includes a body 242 and a needle 244, the body 242 being mounted to the sheath.

The catheter product 236 has a center line 250 which substantially corresponds with a center line of the sheath 238. An opening 252 is formed into the sheath 238, with the lid 240 closing the opening 252. The opening 252 is formed so that the lid 240 is located at an angle of about 45° relative to the center line 250. When the lid 240 is pulled off, a portion 254 of the body 242 is visible, or exposed when viewed in a direction 256 transverse to the center line 250. A person may then contact the portion 254 of the body 242 on a side thereof which is exposed when viewed in the direction 256, and, using a single finger, may remove the catheter product 236 from the sheath 238. The portion 254 may be roughened to increase fictional engagement between the portion 254 and the finger of the person to facilitate removal of the catheter product 236 from the sheath 238.

Figure 13:
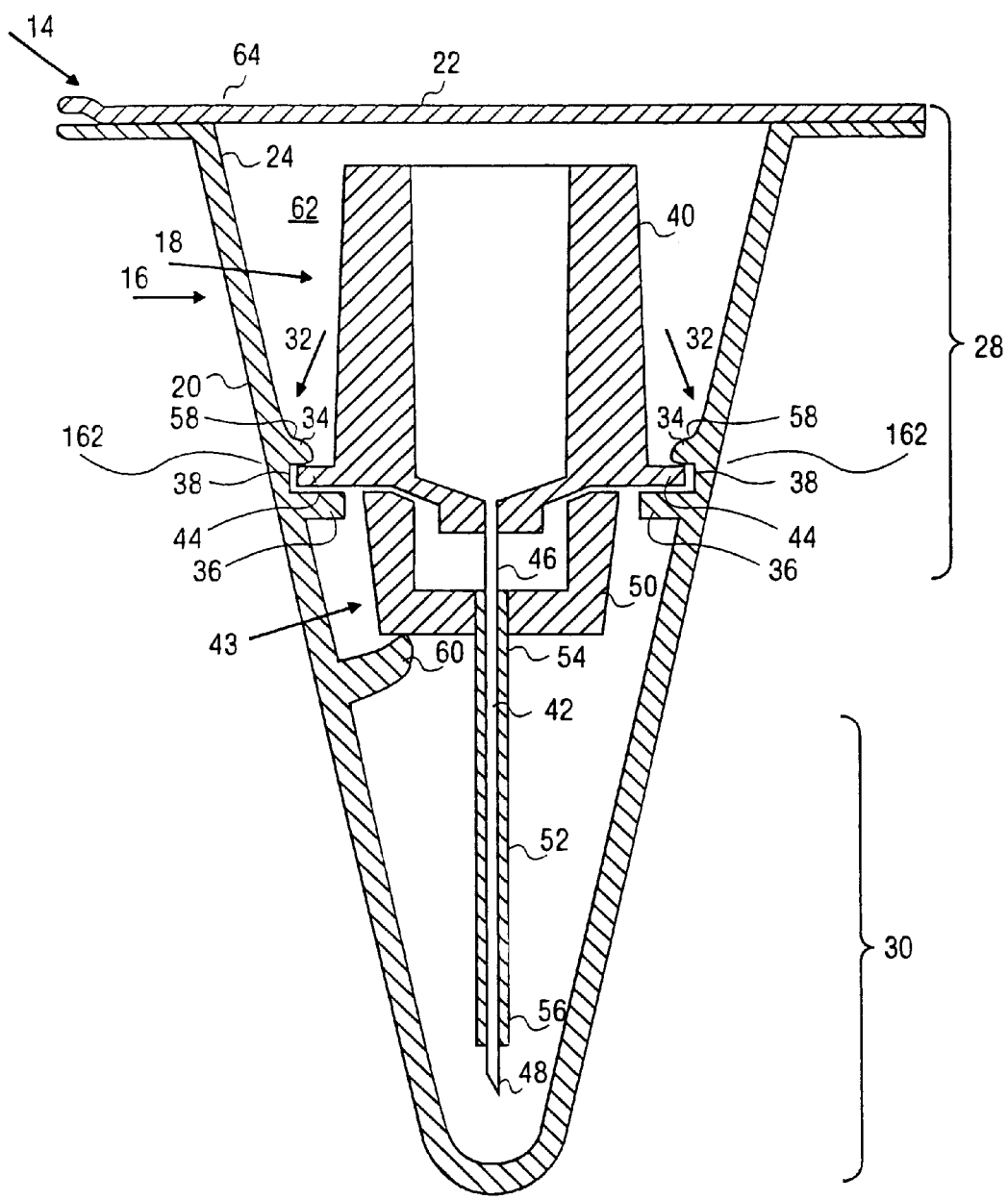
FIG. 13 is a cross-sectional side view of the medical package of FIG. 7.

FIG. 13 illustrates the medical package 14 of FIG. 7 in cross-sectional detail The housing 16 includes an elongate hollow sheath 20 and a lid 22.

The sheath 20 has an opening 24 at the upper end thereof which provides access into the sheath 20. The sheath 20 is relatively large in a first area 28 near the opening 24, and relatively small in a second area 30 on a side of the first area 28 opposing the opening 24.

The sheath 20 has a plurality of retaining formations 32 extending from an inner surface thereof within the first area 28. Each retaining formation 32 includes first and second projections, 34 and 36 respectively, with a gap 38 defined between the first and second projections 34 and 36.

The lid 22 is made of a breathable material which is sold under the name "TYVEK" by Dupont. The breathable material typically has pores which are about 0.2 microns in diameter.

The catheter product 18 includes a body 40, an elongate vascular access member or needle 42, and a catheter assembly 43.

The body 40 has an annular engaging formation 44 extending from an outer surface thereof. The needle 42 has a first end 46 and a second, vascular entry end 48. The first end 46 is secured to the body 40 and second end 48 is located distant from the body.

The catheter assembly 43 includes a hub 50, and a catheter 52. The first end 54 of the catheter 52 is secured to the hub 50 and a second, opposing end 56 of the catheter 52 is located distant from the hub 50. The second end 45 of the needle 42 is inserted through the hub 50, and from the hub 50 through the catheter 52 until the second end 48 of the needle 42 protrudes out of the second end 56 of the catheter 52.

The second end 48 of the needle 42 has a sharp tip which may be used for piercing a vascular such as a vein or an artery. The catheter 52 and the needle 42 are then inserted into the vascular. Fluid within the vascular passes through the needle 42 into the body 40. The body 40 is usually transparent so that the fluid is visible through the body 40. The needle 42 is then removed from the catheter 52 and another device such as a syringe or a pipe of a drip is connected to the hub 50. Fluids can be passed between the other device and the vascular through the hub 50 and the catheter 52.

The medical package 14 is assembled by first inserting the catheter product 18 through the opening 24 into the sheath 20. The needle 42 is inserted first into the sheath 20, followed by the body 40. The first projections 34 are spaced relative to one another more closely than an outer diameter of the engaging formation 44 so that the engaging formation 44 is brought into contact with sloped upper surfaces 58 of the first projections 34. When the catheter product 18 is further inserted into the sheath 20, the engaging formation 44 creates outward forces acting on the sloped upper surfaces 58.

The sheath 20 is made of a flexible material such as polypropylene or nylon and, due to its materials and construction, flexes under the force created by the engaging formation 44 so that the spacing between the first projections 34 widens. Once the spacing between the first projections 34 widens, the engaging formation 44 passes through the first projections 34 and comes to rest against the second projections 36. Due to the flexibility of the sheath 20, the first projections 34 then return to their original positions in a snapping action. Once the first projections 34 then return to their original positions, the engaging formation 44 is locked within the gaps 38.

By locking the engaging formation 44 within the gaps 38, the catheter product 18 is mounted to the sheath 20 and supported in a stationary position relative to the sheath 20. The catheter product 18 is entirely located in the sheath 20 and the sheath 20 is sufficiently strong to protect the catheter product 18. The body 40 is located in the first area 28 of the sheath 20. The needle 42 is almost entirely located in the second area 30 of the sheath 20 with the second end 48 and the sharp tip 56 both displaced from an inner wall of the sheath 20.

A retaining shelf 60 is located on an inner sheath 20. The hub 50 has a surface on opposing sides thereof and the body 30 which rests on the shelf 60. The shelf 60 so prevents the catheter assembly 43 from moving off the needle 42.

The lid 22 is then positioned so that it closes off the opening 24 and is then heated so that a periphery thereof seals circumferentially on a periphery of the opening 24 and is attached to a periphery of the opening 24. The sheath 20 and the lid 22 so jointly define an enclosure 62 which is sealed against ingress of contaminants.

Because of the porous nature of the lid 22, a sterilization fluid such as ethylene oxide gas may be introduced into the enclosure 62 so that the confines of the enclosure 62 may be sterilized. The pores within the lid 22 are, however, generally too small for contaminants or microorganisms to pass through so that the confines of the enclosure 62 remain sterile.

The housing 16 of FIG. 13 provides a rigid and sturdy enclosure which entirely encloses the catheter product 18 and supports the catheter product 18. There is therefore no need for additional packaging such as blister packaging to seal the housing 16 against ingress of contaminants. The medical package 14 can thus be provided to a user substantially in the form shown in FIG. 13.

While certain exemplary embodiments have been described and shown in the accompanying drawings, it is to be understood that such embodiments are merely illustrative and not restrictive of the current invention, and that this invention is not restricted to the specific constructions and arrangements shown and described, since modifications may occur to those ordinarily skilled in the art.

What is claimed:

1. A medical package which includes:
    a housing defining an enclosure which is sealed against ingress of contaminants, and having at least a first part, and a second part which is movable relative to the first part to open the enclosure at least one of the parts having a plurality of pores through which a sterilization fluid can enter the enclosure but which substantially prevent entry of contaminants into the enclosure; and
    a catheter product which includes:
        a body; and
        an elongate vascular access member having a first end and a second, vascular entry end, the first end being secured to the body and the second end being located distant from the body, the catheter product being located entirely within the enclosure, secured in position to the housing and being removable from the housing after the second part is moved relative to the first part to open the enclosure.

2. The medical package of claim 1 wherein the first part is a hollow sheath with an opening providing access into the sheath, the catheter product is at least partially located within the sheath and is secured to the sheath inside the sheath, and the second part is a lid which closes off the opening.

3. The medical package of claim 2 wherein the lid is attached to a periphery of the opening and the attachment between the lid and the periphery of the opening is at least partially breakable.

4. The medical package of claim 2 wherein the enclosure, where defined by the sheath, is relatively large in a first area near the opening and relatively small in a second area on a side of the first area opposing the opening, the body is secured to the sheath in the first area, and the elongate vascular access member is at least partially located in the second area.

5. The medical package of claim 2 wherein the sheath has a retaining formation extending from an inner surface thereof, and the body has an engaging formation which engages with the retaining formation to support the catheter product in position.

6. The medical package of claim 5 wherein the retaining formation includes first and second projections with a gap defined between them, at least one of the projections being movable to the extent that it can give way under a force created by the engaging formation when the catheter product is inserted into the sheath, and at least partially return to its original position so as to lock the engaging formation in the gap.

7. The medical package of claim 5 wherein the sheath is at least partially made of a flexible material, and the retaining formation moves away from the engaging formation when the sheath is flexed, thereby disengaging the engaging formation from the retaining formation so as to allow for removal of the catheter product from the sheath.

8. The medical package of claim 7 which includes finger tabs on opposing sides of the package sheath which, when contacted by two respective fingers on a hand of a person, and moved relative to one another by the fingers, cause movement of the retaining formation away from the engaging formation and disengagement of the engaging formation from the retaining formation.

9. The medical package of claim 8 wherein the retaining formation extends in a first selected direction from the inner surface, and, when the finger tabs are moved relative to one another, the sheath is squeezed together transversely to the first selected direction, causing the retaining formation to move away from the engaging formation in a second selected direction, opposing the first selected direction, and disengagement of the engaging formation from the retaining formation.

10. The medical package of claim 8 which includes flange portions extending from the sheath, and the finger tabs are located on the flange portions.

11. The medical package of claim 10 wherein the flange portions pivot about first portions of the sheath and compress second portions of the sheath towards one another to cause elongation of at least part of the sheath in the second selected direction.

12. The medical package of claim 8 wherein at least a first of the finger tabs pivots about a first portion of the sheath, and the retaining formation is located on a second portion of the sheath, on a side of the first portion approximately opposing the first finger tab, so that, when the first finger tab pivots about the first portion in a first pivoting direction, the retaining formation also pivots in the first pivoting direction about the first portion away from the engaging formation.

13. The medical package of claim 12 wherein the sheath includes an additional retaining formation which engages with a retaining formation of the sheath, a second of the finger tabs pivots about a third portion of the sheath, and the additional retaining formation is located on a fourth portion of the sheath on a side of the third portion approximately opposing the second finger tab so that, when the second finger tab pivots about the third portion in a second pivoting direction, opposing the first pivoting direction, the additional retaining formation also pivots in the second direction away from the additional engaging formation.

14. The medical package of claim 13 wherein the sheath has a hinge portion between the retaining formations which, when the first finger tab pivots in the first pivoting direction and the second finger tab pivots in the second pivoting direction, assists in increasing an amount of rotation of the retaining formations relative to one another, resulting in more movement of the respective retaining formations away from the respective engaging formations.

15. The medical package of claim 14 wherein the hinge portion is formed so as to create a stress concentration which causes more flexing of the sheath.

16. The medical package of claim 14 wherein the hinge portion is a narrowing in the sheath.

17. The medical package of claim 5 wherein the opening has at least two finger wells, on different sides of the catheter product, into which fingers on a hand of a person are insertable, the finger wells being open towards the catheter product to allow for gripping of the catheter product and subsequent removal of the catheter product from the sheath.

18. The medical package of claim 5 wherein the sheath has first and second opposed wall portions having edges which partially define the opening, and the lid closes off the opening, wherein the edges are shaped so that, when the lid is at least partially moved to open the enclosure, there is a line of sight through the sheath between the wall portions of the sheath, the line of sight being at least partially blocked by the catheter product.

19. The medical package of claim 5 wherein the opening is formed so that, when the lid is at least partially moved to open the enclosure, a portion of the medical product is exposed when viewed in a direction at right angles to a center line of the medical product.

20. The medical package of claim 5 wherein the second part is a lid which closes the opening, the lid having a plurality of pores through which a sterilization fluid can enter the enclosure.

21. The medical package of claim 5 wherein the sheath has at least first and second components wherein, when the lid is at least partially removed, the second component is movable relative to the first component to allow for better access to the medical product.

22. The medical package of claim 21 wherein the retaining formation is located on an inner wall of the sheath, and the body has an engaging formation which engages with the first component wherein, when the second component is moved relative to the first component to allow for better access to the medical product, the engaging formation is engaged with the retaining formation.

23. The medical package of claim 21 wherein the second component hinges relative to the first component.

24. The medical package of claim 23 wherein the sheath has at least a third component which hinges relative to the first component to allow for better access to the medical product.

25. The medical package of claim 1 wherein at least one of the parts has a plurality of pores through which a sterilization fluid can enter the enclosure.

26. The medical package of claim 1 wherein the second end of the elongate vascular access member is displaced from an inner wall of the housing.

27. The medical package of claim 1 wherein the elongate vascular access member has a sharp tip at the second end.

28. The medical package of claim 1 wherein the vascular access member is a needle and the second end is a sharp tip of the needle, the medical package further including:
   a catheter assembly comprising:
      a hub; and
      a catheter having a first end secured to the hub and a second end located distant from the hub, the hub and the catheter being located over the needle with the catheter located on a side of the hub opposing the body, the housing further having a shelf on an inner surface thereof, the shelf supporting the hub on a surface thereof opposing the body.

29. A medical package which includes:
   a housing defining an enclosure which is sealed against ingress of contaminants, and having a hollow elongate sheath with an end having an opening into the sheath, and a lid which closes the opening and seals with a periphery of the opening;
   a catheter product including:
      a body; and
      an elongate vascular access member having a first end and a second, vascular entry end, the first end being secured to the body and the second end being located distant from the body, the catheter product being located entirely within the sheath.

30. A medical package which includes:
   a housing defining an enclosure which is sealed against ingress of contaminants, the housing including at least:

a flexible first part having a retaining formation extending from an inner surface thereof; and a second part which is movable relative to the first part to open the enclosure; and a catheter product including:

a body having an engaging formation thereon;

an elongate vascular access member having a first end and a second, vascular entry end, the first end being secured to the body and the second end being located distant from the body, the catheter product being located entirely within the enclosure, secured in position to the housing by interengagement of the engaging formation with the retaining formation, wherein flexing of the first part causes disengagement of the engaging formation from the retaining formation to allow for removal of the catheter product from the housing after the second part is moved relative to the first part to open the enclosure.

31. A method of packaging a catheter product comprising:

locating the catheter product within a housing which defines an enclosure which is sealed against ingress of dirt so that the medical product is located entirely within the enclosure, the housing including at least one part having a plurality of pores through which a sterilization fluid can enter the enclosure, but which substantially prevent entry of contaminants into the enclosure, the medical product having a body secured in position to the housing, and an elongate vascular access member having a first end and a second, vascular entry end, the first end being secured to the body and the second end being located distant from the body in a position which is displaced from an inner wall of the housing.

* * * * *